United States Patent
Ashwood et al.

(10) Patent No.: US 8,168,799 B2
(45) Date of Patent: May 1, 2012

(54) PROCESS FOR THE PREPARATION OF TETRAZOLYTETRAHYDROCYCLO-PENTAPYRAZOLES

(75) Inventors: Michael Stewart Ashwood, Bishop's Stortford (GB); Matthew Bio, Boston, MA (US); Edward Cleator, Cambridge (GB); David Hands, Enfield (GB); Faye Julia Sheen, Hertford (GB); Robert Darrin Wilson, Enfield (GB)

(73) Assignee: Merck Sharpe & Dohme Ltd., Hoddesdon, Hertfordshire (GB)

( * ) Notice: Subject to any disclaimer, the term of this patent is extended or adjusted under 35 U.S.C. 154(b) by 550 days.

(21) Appl. No.: 11/919,309

(22) PCT Filed: Apr. 20, 2006

(86) PCT No.: PCT/GB2006/001446
§ 371 (c)(1),
(2), (4) Date: Nov. 25, 2009

(87) PCT Pub. No.: WO2006/114581
PCT Pub. Date: Nov. 2, 2006

(65) Prior Publication Data
US 2010/0174091 A1    Jul. 8, 2010

Related U.S. Application Data

(60) Provisional application No. 60/676,334, filed on Apr. 29, 2005.

(30) Foreign Application Priority Data

Apr. 28, 2005 (GB) .................................. 0508515.4

(51) Int. Cl.
*C07D 403/04* (2006.01)
(52) U.S. Cl. ........................................ 548/253; 548/254
(58) Field of Classification Search ........................ None
See application file for complete search history.

(56) References Cited

FOREIGN PATENT DOCUMENTS

| EP | 0 529 854 A2 | 3/1993 |
|---|---|---|
| WO | WO 2005/044816 A1 | 5/2005 |
| WO | WO 2007/015111 A1 | 2/2007 |

OTHER PUBLICATIONS van Herk et al., J. Med. Chem., vol. 46, pp. 3945-3951 (2003).
Geen et al., Synthetic Communications, vol. 27(6), pp. 1065-1073 (1997).

*Primary Examiner* — Kamal Saeed
(74) *Attorney, Agent, or Firm* — Dianne Pecoraro; Catherine D. Fitch

(57) ABSTRACT

A process for the preparation of a compound of formula (I), or a salt, hydrate or solvate thereof; wherein $R^1$ and $R^2$ are each independently hydrogen, or $C_{1-6}$ alkyl groups or $R^1$ and $R^2$ are linked and, together with the cyclopentane carbon atoms to which they are attached, form a cyclopropyl ring.

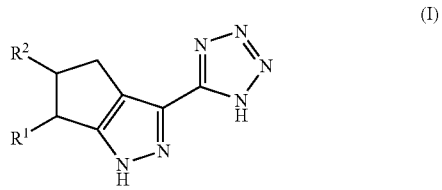

(I)

12 Claims, No Drawings

PROCESS FOR THE PREPARATION OF TETRAZOLYTETRAHYDROCYCLO-PENTAPYRAZOLES

PRIORITY CLAIM

This application is a §371 application of PCT/GB2006/001446 that was filed on Apr. 20, 2006, which claims priority from the Great Britain Provisional Application No.: 0508515.4 filed on Apr. 28, 2005, and U.S. Provisional Application No.: 60/676,334 filed on Apr. 29, 2005.

The present invention relates to the preparation of tetrazole derivatives, more specifically cyclopentanepyrazole tetrazole derivatives.

Tetrazolyltetrahydrocyclopentapyrazoles have been shown to demonstrate useful pharmacologic properties, for example as agonists for the nicotinic acid receptor, RUP25. Thus, patent application PCT/US2004/035927 discloses substituted pyrazole tetrazole derivatives having useful pharmacological properties and in particular, compounds of the formula (A):

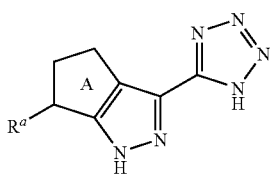

(A)

where $R^a$ is H or OH and ring A is optionally substituted with one or two substituents selected from halo, $C_{1-4}$alkyl, $C_{1-4}$alkoxy, and $C_{3-5}$cycloalkyl, or a pharmaceutically acceptable salt, solvate or hydrate thereof.

A number of methods are disclosed for preparing compounds of the formula (A) but all these methods involve formation of the tetrazole ring in one of the last steps by the reaction of a tetrahydrocyclopentapyrazole carbonitrile with an azide such as sodium azide, e.g

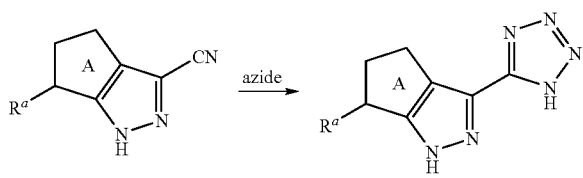

Most of these methods involve multiple steps, and consequently give relatively low final yields of the tetrazole based on the cycloalkanone starting material. In addition, the use of azides such as sodium azide involves safety hazards and is preferably to be avoided, particularly if reactions are to be carried out on a multimolar scale.

We have now discovered that tetrazolyltetrahydrocyclopentapyrazoles can be prepared in good yield in a two-step process from the relevant cyclopentanone utilising the pre-formed tetrazole without the need for sodium azide in the process. The final step of this process involves the reaction of a cyclopentane diketone derivative with hydrazine. However, it has been found that it is not necessary to isolate this diketone intermediate and that the process can be carried out as a one-pot process.

Accordingly, in one aspect, the present invention provides a process for the preparation of a compound of the formula (I):

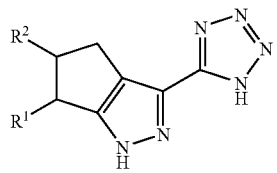

(I)

or a salt, hydrate or solvate thereof;
which process comprises the reaction of a compound of the formula (II):

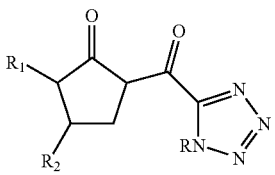

(II)

or a tautomer, thereof; wherein R is hydrogen or a protecting group, or a metal ion; $R^1$ and $R^2$ are each independently hydrogen, or $C_{1-6}$ alkyl groups or $R^1$ and $R^2$ are linked and, together with the carbon atoms to which they are attached, form a cyclopropyl ring; with hydrazine, and thereafter removing any protecting groups which may be present.

Suitable protecting groups include benzyl, phenethyl, diphenylmethyl, trityl and substituted benzyl and phenethyl groups such as p-nitrobenzyl, p-methoxybenzyl and p-methylbenzyl. Removal of the protecting group may be carried out under standard conditions, for example, when the protecting group is benzyl or substituted benzyl by hydrogenation in the presence of a catalyst, for example palladium on carbon based catalysts, more specifically palladium black.

Certain compounds of the formula (I) may exist as enantiomers. The present invention provides for the preparation of single enantiomers, by starting with an enantiomerically pure compound of the formula (II), as well as mixtures of enantiomers, which may in turn be separated by methods well known to those skilled in the art.

The compound of the formula (II) may be present in a protected form, as the neutral form or as a salt, for example a salt with one or two alkali metal ions (eg. a disodium salt or a sodium potassium bis-salt).

The reaction is conveniently carried out in a suitable solvent, e.g. an aqueous solvent such as water or a mixture of water with a $C_{1-4}$ alcohol, for example methanol, ethanol or isopropanol, or with a polar aprotic solvent, such as dimethyformanide (DMF) under acidic conditions at a non-extreme temperature, for example between −20° C. and 100° C. and suitably between −10° C. and 50° C., conveniently at ambient temperature (5° C.-25° C.). The hydrazine may be present as aqueous hydrazine hydrate, in which case no additional solvent is required other than the water present, but acid may be required to catalyse the reaction, for example a mineral acid such as hydrochloric acid, an organic acid such as acetic acid or trifluoroacetic acid or a sulfonic acid such as methane sulfonic acid. When the compound of the formula (II) is present as a salt, acid will be required and it is preferably present even when the compound of the formula (II) is present as the diketone. Alternatively, the hydrazine may be present as an acid addition salt, in which case no acid will be required but solvent will be required to solubilise the reactants.

The compound of the formula (I) may be isolated from the reaction mixture at acid pH, conveniently at a pH in the range of 0 to 5.

The present invention also provides a compound of the formula (II) or tautomer thereof, as hereinbefore defined, including neutral forms, salts and enantiomers of compounds of the formula (II), useful in the preparation of compounds of the formula (I).

In a further embodiment of the invention, the compound of the formula (II) may be prepared by the reaction of a cyclopentanone of the formula (III):

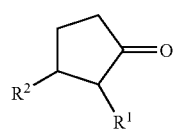
(III)

or an enantiomer thereof, with a compound of the formula (IV):

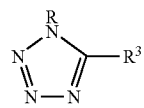
(IV)

in the presence of a base; wherein R is as hereinbefore defined;
$R^1$ and $R^2$ are each independently hydrogen, or $C_{1-6}$ alkyl groups or $R^1$ and $R^2$ are linked and, together with the cyclopentanone carbon atoms to which they are attached form a cyclopropyl ring, and $R^3$ is a suitable carboxylic acid derivative.

Suitably Wand $R^2$ are hydrogen or are linked to give a cyclopropyl ring fused to the cyclopentane ring. Suitable carboxylic acid derivatives $R^3$ are those of the formula CO.L in which a leaving group L may be displaced without affecting the stability of the starting tetrazole or resulting diketone of the formula (II), for example an ester in which L is suitably $C_{1-4}$ alkoxy or benzyloxy and preferably ethoxy.

The tetrazole (IV) may conveniently be utilised in the form of a salt, suitably an alkaline or alkaline earth metal salt such as the sodium or magnesium salt. The reaction is suitably carried out under anhydrous conditions in a polar aprotic solvent. The reaction is conveniently carried out at a non-elevated temperature, for example –20° C. to 20° C., suitably –20° C. to 0° C. and preferably at around –10° C. Suitable solvents include dimethylformamide (DMF), dimethylacetamide (DMAC) dimethylsulfoxide (DMSO), N-methylpyrrolidinone (NMP), and hexamethylphosphorimidic triamide (HMPT) as well as tetrahydrofuran (THF). In one embodiment of the invention, DMF has been found to be preferred. Suitable bases for use in the reaction are those that are soluble in the solvent, can remove a proton from the cyclopentanone but do not otherwise participate in the reaction. Strong organic bases such as 1,8-diazabicyclo[5.4.0]undec-7-ene (DBU), diazabicyclo[4.3.0]non-5-ene (DBN), tetramethylguanidine or alkali or alkaline earth metal bases, such as sodium or magnesium alkoxides, and particularly potassium tert-butoxide, are preferred.

In one embodiment of the invention, the tetrazole (IV) is first dissolved in solvent and base added. The cycloalkanone of formula (III) is then added slowly so that the concentration of unreacted cycloalkanone is kept low in the reaction mixture.

The compound of the formula (II) may suitably be isolated, when it is present as the bis-salt, by adding a solvent in which the compound of the formula (II) is insoluble or sparingly soluble, and filtering off the precipitate. Isopropyl acetate, acetonitrile and tetrahydrofuran are suitable solvents, and isopropyl acetate is preferred. Alternatively, other standard work-up procedures for obtaining desired products from reaction mixtures may be employed.

In a further embodiment, the present invention provides a one-pot process for the preparation of a compound of the formula (I) from a compound of the formula (II) which process comprises the reaction of a compound of the formula (III) with a compound of the formula (N) followed by reaction of the intermediate compound of the formula (II) in-situ with hydrazine, where compounds of the formula (I), (II), (III) and (IV) are as hereinbefore defined.

The reaction of the compound (III) with a compound of the formula (IV) is carried out under the conditions described above, eg. in a polar aprotic solvent in the presence of a base. In one embodiment of the invention, DMF and potassium tert-butoxide are the preferred solvent and base respectively. This reaction step is most suitably carried out at –20° C. to 0° C. and preferably at –10° C. to –5° C. In a preferred embodiment, the tetrazole (IV), which may be present in the form of a salt, is first dissolved in solvent and base added, followed by slow addition of cycloalkanone of formula (III) so that the concentration of unreacted cycloalkanone is minimised.

Similarly, the conditions for the second step of the process are as described above for the reaction of a compound of the formula (II) with hydrazine. Acid, for example a mineral acid such as hydrochloric acid, or organic acid, such as acetic acid, is conveniently added to acidify the reaction mixture and hydrazine added, for example in the form of hydrazine hydrate. The reaction is conveniently carried out at –10° C. to 50° C. and suitably between 5° C. and 20° C.

The reaction mixture is conveniently worked up by removing the solvent by evaporation, dissolving the residues in hot water and acidifying the resultant solution, for example with a mineral acid such as hydrochloric acid, and filtering off the resultant compound of the formula (I).

The following examples illustrate the invention and the manner in which it may be performed:

EXAMPLE 1

Preparation of Tetrazolyltetrahydrocyclopentapyrazole (Two-Step, One Pot Process)

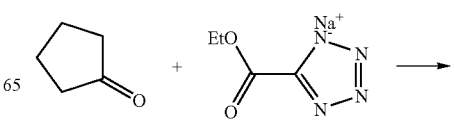

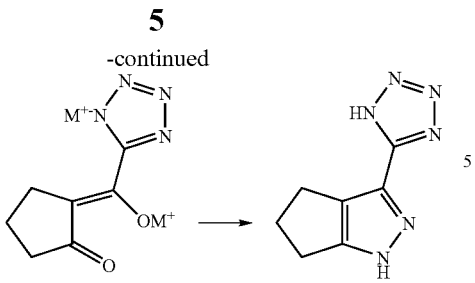

The tetrazole ester sodium salt (15.74 g, 96.5 mmol) was dissolved in DMF (140 mL) and the solution cooled to −10° C. Potassium tert-butoxide (13.48 g, 120 mmol) was added, maintaining the temperature ≦0° C.). The mixture was re-cooled to −10° C. and a solution of cyclopentanone (7.08 mL, 80 mmol) in DMF (40 ml) was added over 2 h maintaining the temperature ≦−8° C. The resulting mixture was then aged for another hour at this temperature.

1M Hydrochloric acid (19.8 mL) was added slowly followed by 55% hydrazine hydrate (8.7 mL, 96 mmol) maintaining the temperature ≦5° C.). The cooling bath was removed and the reaction mixture was allowed to warm to ambient temperature overnight.

The reaction mixture was evaporated to dryness and flushed with water (100 mL). The residue was dissolved in hot water (475 mL) and the resulting solution acidified to pH 3 with conc. HCl (7.5 mL). The resulting slurry was aged at ambient temperature for 2 hours. The precipitate was collected by filtration and washed with water (150 mL). After drying in vacuo overnight at 45° C., the title compound (11.48 g) was isolated as a pale yellow crystalline solid in 81% yield. Melting point 271° C.

EXAMPLE 2

Preparation of Tetrazolyltetrahydrocyclopentapyrazole (Two-Step, Two Pot Process)

a) Preparation of the diketone bis-salt

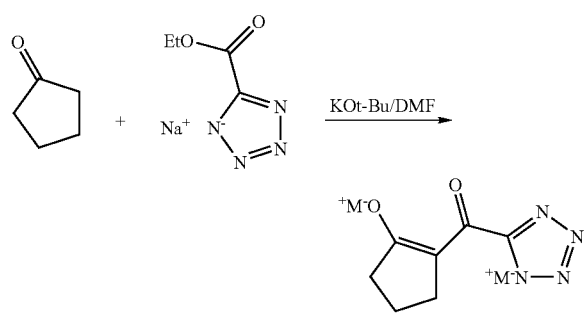

1H-tetrazole-5-carboxylic acid ethyl ester sodium salt (16.40 g, 100 mmol) and cyclopentanone (10.95 g, 130 mmol) were charged to a 1 L vessel under a nitrogen atmosphere. DMF (100 mL) was added to dissolve the reagents at room temperature. The resulting solution was cooled to 0° C. and a solution potassium tert-butoxide (16.9 g) in DMF (65 mL) was added dropwise over 30 min, giving an off-white slurry. The slurry was stirred at 0-5° C. for 1 hour when the reaction was complete according to HPLC analysis. The slurry was diluted with isopropyl acetate (165 mL) and stirred at 0-5° C. for 1 hour. The solid was then filtered and washed with a 1:1 mixture of DMF and isopropyl acetate (20 mL), followed by isopropyl acetate (2×20 mL). The solid was dried to give the title compound as an off-white solid (25 g).

b) Preparation of tetrazolyltetrahydrocyclopentapyrazole

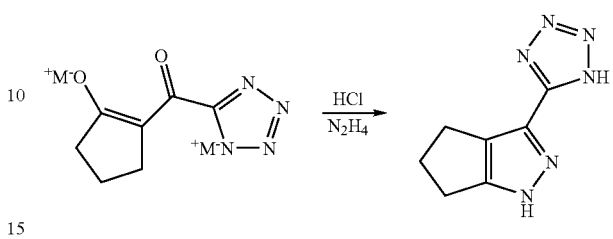

The isolated diketone bis-salt (18 g) was dissolved in water (90 mL) at room temperature and the solution was cooled to 0° C. 2N HCl (90 mL) was added giving an off-white precipitate. This slurry was again cooled to 0° C. and 35% hydrazine (6.0 mL) was added. The mixture was warmed to room temperature and stirred until the reaction was completed according to HPLC analysis. The solid was filtered, washed with water (20 mL) and dried in vacuo at 35° C., providing the title compound as an off-white solid (6.0 g) in approximately 47% yield (from cyclopentanone).

EXAMPLE 3

Preparation of (4aR,5aR)-3-(2H-tetrazol-5-yl)-4,4a,5,5a-tetrahydro-1H-cyclopropa[4,5]cyclopenta[1,2-c]pyrazole a) Preparation of Alcohol 2.

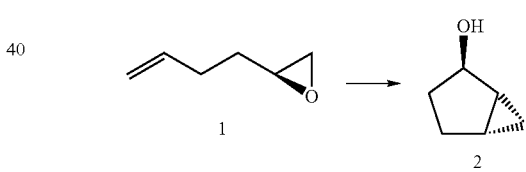

R-(+)-Epoxide (1) (100 g, 1.019 mol) was dissolved in dry tert-butylmethyl ether MTBE (1 L). To this solution was added 2,2,6,6-tetramethylpiperidine (71.96 g, 0.509 mol) and the reaction mixture was cooled to between −5 and 0° C. n-HexLi (2.3M in hexanes, 487 mL, 1.121 mol) was added over 4 hours keeping the temperature below 0° C. The resulting solution was aged at this temperature until all the starting epoxide was consumed according to GC analysis(approximately 4 hours). The reaction mixture was carefully quenched by the addition of 3N HCl (543 mL) whilst maintaining the internal temperature <0° C. The aqueous phase was separated and the organic phase washed with 3N HCl (170 mL). The combined aqueous layers were back extracted with MTBE (500 mL and 250 mL). The combined organic extracts were then concentrated to a total volume of approximately 450 mL. The final organic layer contained 84.8 g of compound 2 (86% yield) according to GC analysis. The resulting product stream was then used in the following oxidation reaction.

b) Preparation of Ketone 3

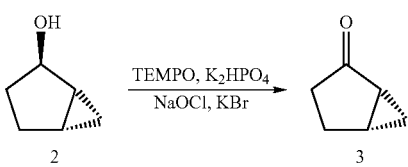

To the MTBE solution of bicyclic alcohol 2 (76.89 g, 0.783 mol) was added an aqueous solution of dipotassium hydrogenphosphate (204.7 g, 1.175 mol) in water. Potassium bromide (13.98 g, 0.118 mol) was charged as solid and the resulting biphasic mixture agitated at 0° C. To this mixture was added TEMPO (1.29 g, 0.008 mol), followed by a slow addition of 10.8 wt % sodium hypochlorite (527 mL, 0.964 mol) over 2 hours, whilst maintaining the temperature between 0 and 5° C. The conversion of the alcohol 2 was monitored by GC analysis and upon complete consumption, the reaction was quenched by addition of 2M sodium sulfite solution until all excess oxidant was destroyed as determined by starch iodide indicator paper. The reaction was warmed to ambient temperature and the aqueous layer separated. The aqueous layer was back extracted with MTBE (2×100 mL). The combined organic extracts were dried over 3 Å molecular sieves overnight. The sieves were removed by filtration and the filtrate concentrated in vacuo to an approximately 50 wt % solution, which according to HPLC analysis contained 65.5 g of ketone 3 (87% yield). Vacuum distillation (70-80° C. at 50-60 mmHg) provided a 96% recovery of the available ketone.

c) Acylation—Condensation:

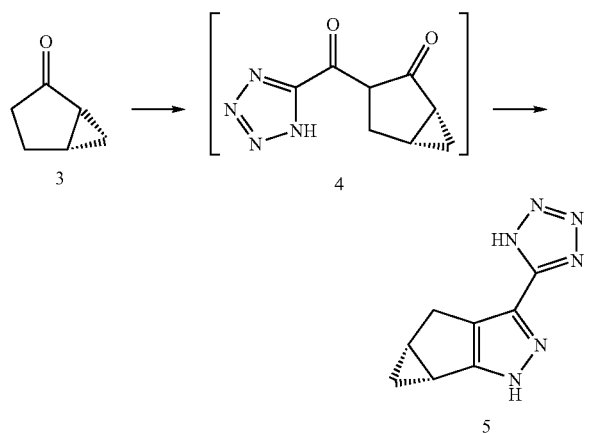

The distilled ketone 3 (20 g, 0.208 mol) as a solution in DMF (20 mL) was added dropwise over 2-3 h to a cold (−10° C.) solution of the tetrazole ester sodium salt (40.97 g, 0.25 mol) and potassium tert-butoxide (32.69 g, 0.291 mol) in DMF (180 mL) maintaining the internal temp at <−5° C. At the end of addition the reaction was stirred at ~0° C. until complete consumption of the ketone was accomplished according to HPLC analysis. To the reaction mixture was added 35 wt % hydrazine hydrate (20.2 mL, 0.229 mol) followed by concentrated HCl (46.12 mL, 0.562 mol) whilst maintaining the temperature <10° C. The resulting slurry was left to stir at overnight at room temperature to achieve complete conversion of 4 to 5. The reaction mixture was concentrated to a low volume by repeated vacuum distillation with the addition of water. During this operation product 5 crystallized. The pH was adjusted to 3 with concentrated HCl. The slurry was aged for 2-3 h, filtered and the solid cake was washed with water. After drying at 50° C. in vacuo overnight, 33.5 g of the title compound was obtained in 80% corrected yield. The mother liquors assayed for 1.4 g of product for an overall chemical yield of 83%. Melting point 231° C.

EXAMPLE 4

Preparation of Tetrazolyltetrahydrocyclopentapyrazole a) Preparation of $N^1$ and $N^2$-benzyl tetrazole

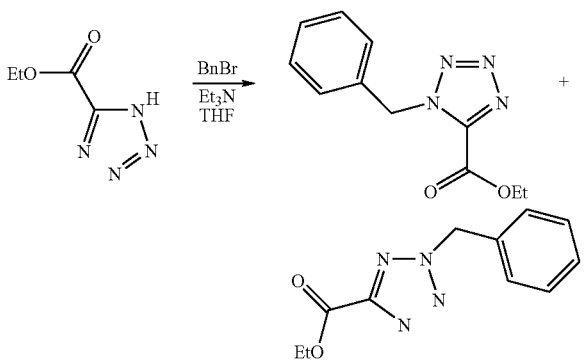

Benzyl bromide (2.3 mL, 19.36 mmol) was added to a stirred solution of tetrazole ester sodium salt (1.8 g, 17.6 mmol) and triethylamine (2.69 mL, 19.36 mmol) under a nitrogen atmosphere and the reaction mixture aged at ambient temperature overnight. The suspension was diluted with water (15 mL) and ethyl acetate (25 mL). The layers were separated and the aqueous layer was extracted with EtOAc (50 mL). The combined organic layers were dried ($Na_2SO_4$), filtered and concentrated to give 2.33 g of a mixture of the title compounds as a colourless oil in 86% yield.

b) Preparation of Diketone

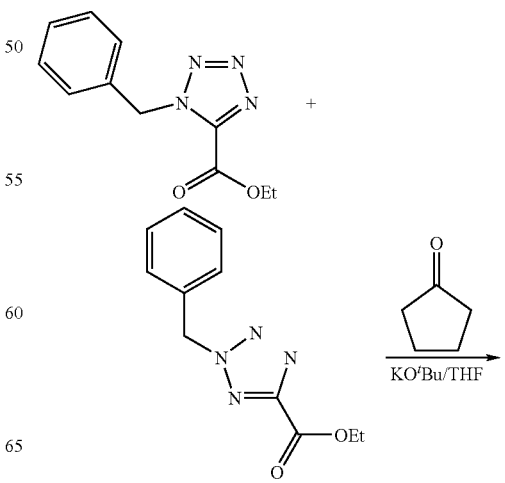

-continued

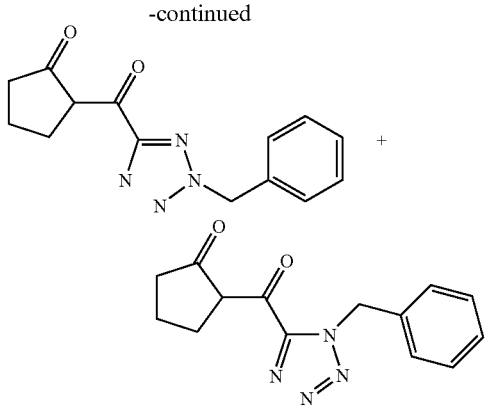

To a solution of the mixture of benzylated tetrazole esters (15 g, 64 mmol) and cyclopentanone (5.13 mL, 58 mmol) in THF (116 mL) at 0° C. was added a 1M potassium tert-butoxide solution in THF (58 mL, 58 mmol) dropwise over 150 min., under a nitrogen atmosphere, whilst maintaining the temperature at 0° C. The mixture was aged for a further 2 h at this temperature and then quenched by the addition of 2M HCl (25 mL). Water (150 mL) and ethyl acetate (200 mL) were added and the layers separated. The aqueous layer was extracted with ethyl acetate (150 mL). The combined organic layers were dried ($Na_2SO_4$), filtered and concentrated to give 15 g of an orange oil which was purified by flash column chromatography (using 2:1 hexane:ethyl acetate to elute) to give the diketone (12.02 g) as a mixture of isomers in 64% yield.

c) Preparation of Pyrazole

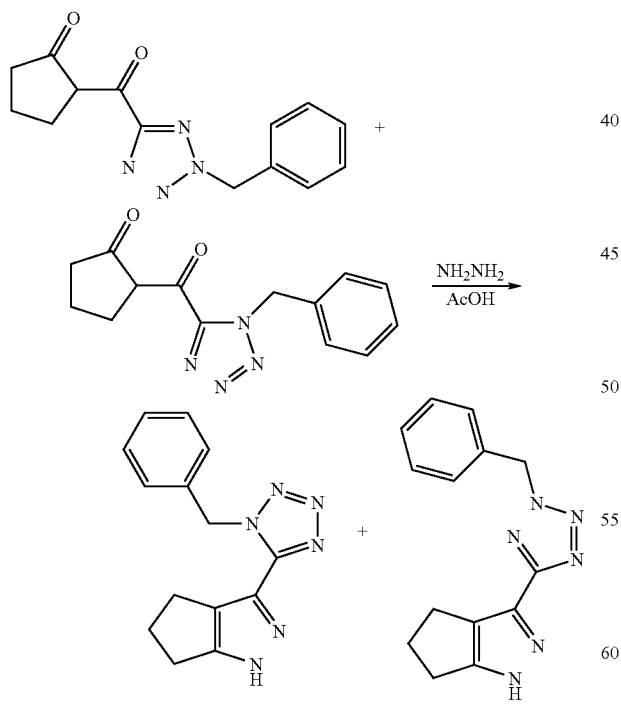

The mixture of benzylated diketone isomers (2 g, 7.4 mmol) was dissolved in acetic acid (20 mL) and hydrazine hydrate (0.426 mL, 7.4 mmol) was added dropwise over 30 min. The reaction was heated to 50° C. for 4 h and then cooled to room temperature. The acetic acid was evaporated in vacuo to give 2.8 g of a yellow oil which was a mixture of regioisomers according to NMR.

d) Preparation of N—H Tetrazole

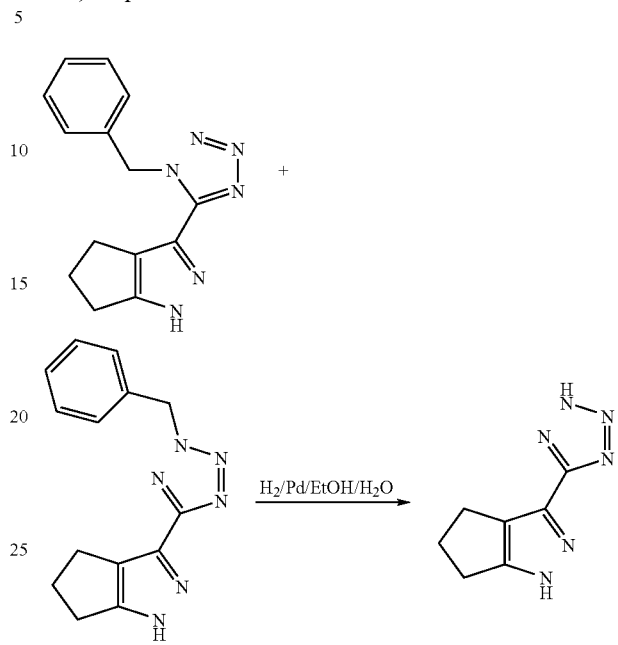

A mixture of the benzylated tetrazole isomers (50 mg, 0.19 mmol) was dissolved in water (1 mL) and ethanol (1 mL) and palladium black catalyst (30 mg) was added in one portion. The reaction mixture was stirred under an 85 psi atmosphere of hydrogen at 60° C. for 18 h. Filtration of the catalyst and evaporation in vacuo gave 30 mg of the title compound as an off-white solid in 90% yield:

The invention claimed is:
1. A process for the preparation of a compound of formula (I):

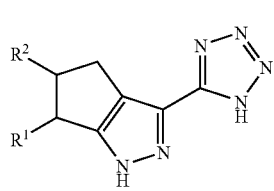

(I)

or a salt, hydrate or solvate thereof;
which process comprises the reaction of a compound of the formula (II):

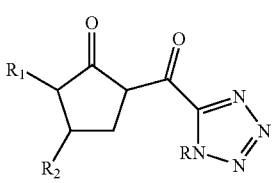

(II)

or a tautomer thereof; wherein R is hydrogen or a protecting group, or a metal ion; $R^1$ and $R^2$ are each independently hydrogen, or $C_{1-6}$ alkyl groups or $R^1$ and $R^2$ are linked and, together with the carbon atoms to which they are attached, form a cyclopropyl ring; with hydrazine, and thereafter removing any protecting groups which may be present.

2. A process according to claim 1, wherein the reaction is carried out in an aqueous or a polar aprotic solvent.

3. A process according to claim 1, wherein the reaction is carried out at a temperature of −20 ° C. to 100 ° C.

4. A process according to claim 1, wherein the hydrazine is present as aqueous hydrazine hydrate, optionally in the presence of an acid.

5. A process according to claim 2, wherein the hydrazine is present as an acid addition salt.

6. A compound of formula (II) as defined in claim 1.

7. A process for the preparation of a compound of formula (II) defined in claim 1 by the reaction of a cyclopentanone of the formula (III):

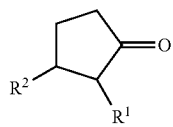

(II)

or an enantiomer thereof, with a compound of formula (IV):

(IV)

in the presence of a base; wherein R, $R^1$ and $R^2$ are as defined in claim 1; and $R^3$ is a suitable carboxylic acid derivative.

8. A process according to claim 7, wherein the reaction is carried out under anhydrous conditions in a polar aprotic solvent.

9. A process according to claim 7, wherein the reaction is carried out at a temperature of −20 ° C. to 20 ° C.

10. A process according to claim 7, wherein the cyclopentanone of formula (III) is slowly added to the compound of formula (IV) and base to keep the concentration of unreacted cycloalkanone low in the reaction mixture.

11. A one-pot process for the preparation of a compound of the formula (I) from a compound of the formula (III) which process comprises the reaction of a compound of the formula (III) with a compound of the formula (IV) followed by reaction of the intermediate compound of the formula (II) in-situ with hydrazine, where compounds of the formulae (I), (II), (III) and (IV) are as defined in claim 7.

12. A process according to claim 1 wherein, $R^1$ and $R^2$ are hydrogen or are linked to give a fused cyclopropyl ring.

* * * * *